US00PP09629P

United States Patent [19]

Schreurs

[11] Patent Number: Plant 9,629

[45] Date of Patent: Aug. 20, 1996

[54] FLORIBUNDA ROSE PLANT NAMED 'SCHOVIAN'

[75] Inventor: Petrus N. J. Schreurs, De Kwakel, Netherlands

[73] Assignee: Piet Schreurs Holding B.V., De Kwakel, Netherlands

[21] Appl. No.: 523,825

[22] Filed: Sep. 6, 1995

[51] Int. Cl.[6] ..... A01H 5/00

[52] U.S. Cl. ..... Plt./23

[58] Field of Search ..... Plt./23, 24, 22

*Primary Examiner*—Howard J. Locker
*Attorney, Agent, or Firm*—Foley & Lardner

[57] ABSTRACT

A new rose plant of the Floribunda Class named 'Schovian,' characterized by good flower production throughout the year; white (RHS 155B), simultaneously opening flowers borne in clusters; 3 to 12 flowers per cluster; generally thornless; vigorous upright growth; good vase life; more than 90% of the flowering stems have flowers borne in clusters.

4 Drawing Sheets

The present invention comprises a new and distinct cultivar of rose plant of the Floribunda Class, hereinafter referred to by the cultivar name 'Schovian.'

'Schovian' is a product of a planned breeding program having the objective of creating new Floribunda Class rose cultivars with characteristics ideally suited for the production of cut flowers; good production of white, simultaneously opening flowers borne in clusters; production of more than 90% sprays throughout the year; and a vigorous upright growth habit. It is understood that 90% sprays throughout the year means that more than 90% of the flowering stems have flowers borne in clusters (perfect spray rose) and less than 10% of the flowering stems have only one single flower.

'Schovian' was originated from a hybridization made by Petrus N. J. Schreurs in a controlled breeding program in De Kwakel, The Netherlands, in 1987. The female parent was the variety 'Interprince' (U.S. Plant Pat. No. 8,102). The male parent was an unnamed Piet Schreurs De Kwakel B.V. proprietary seedling having small, pink, simultaneously opening flowers borne in clusters and very few thorns.

'Schovian' was discovered and selected as one flowering plant within the progeny of the stated parentage by Petrus N. J. Schreurs, in February, 1989, in a controlled environment in De Kwakel, The Netherlands. Asexual reproduction of the new cultivar by budding and cuttings, as performed by Petrus N. J. Schreurs in De Kwakel, The Netherlands, has demonstrated that the combination of characteristics, as herein disclosed for 'Schovian,' are firmly fixed through successive generations of asexual reproduction.

'Schovian' has not been observed under all possible environmental conditions. Phenotype may vary significantly with variations in environment, such as temperature, light intensity, and daylength, without any changes in genotype.

The following traits have been repeatedly observed and are determined to be basic characteristics of 'Schovian,' which in combination, distinguish this rose as a new and distinct cultivar:

1. Vaselife of 10 to 12 days.
2. Good flower production throughout the year (more than 200 flowers per square meter).
3. White, simultaneously opening flowers borne in clusters.
4. Flowers are in clusters, with 3–12 flowers per stem.
5. Flowers having 25 to 35 petals.
6. 'Schovian' is generally thornless.
7. No unusual susceptibility to fungal pathogens.
8. Vigorous upright growth habit.

9. More than 90% of the flowering stems have flowers borne in clusters throughout the year.

Of the many commercial cultivars known to the present inventor, the most similar in comparison to 'Schovian' is 'Interprince,' a white spray rose described in U.S. Plant Pat. No. 8,102. Chart A compares certain characteristics of 'Schovian' to those same charcteristics of 'Interprince.'

In general comparison to 'Interprince,' 'Schovian' has no thorns. With regard to flowers, the petal color of 'Schovian' is more greenish-white than 'Interprince.' The 'Interprince' petal color is more yellowish-white than 'Schovian.' 'Schovian' has more oval-shaped leaflets. The average stem length of 'Interprince' is longer than 'Schovian' and 'Schovian' has smaller flowers than 'Interprince.' The flowers on each stem of 'Schovian' grow more or less to the same height while the flowers on each stem of 'Interprince' grow to different heights.

The accompanying color photographic drawings show the typical inflorescence and foliage characteristics of 'Schovian,' with colors as nearly true as possible with illustrations of this type.

Sheet 1 is a single stem of 'Schovian.'

Sheet 2 is a comparison of one stem of 'Schovian' and 'Interprince.'

Sheet 3 is a comparison of different plant parts from 'Schovian' and 'Interprince.'

Sheet 4 is a detailed view of several parts of 'Schovian.' The photos were made in De Kwakel, The Netherlands in a greenhouse with a light intensity of about 2.40 Klux.

In the following description, color references are made to The Royal Horticultural Society (R.H.S.) Colour chart. The color values were determined between 10:00 a.m. and 12:00 noon on Jun. 29, 1994, under 2.40 Klux, in De Kwakel, The Netherlands.

Classification:

*Botanical.*—*Rosa hybrida,* cv. 'Schovian.'
*Commerical.*—Floribunda, spray rose.

PLANT:

General appearance:

*Habit.*—Upright growth habit.
*Growth.*—Vigorous.
*Average stem length.*—Length of 50 to 60 cm.
*Thorns.*—None or occasional thorns.
*Wood.*—New wood is light green and smoth, old wood is green, frequently brown longitudinal stripes on bark.

Foliage:

*Leaves.*—Number: Normal mid-stem leaves have 5 to 7 leaflets. Shape leaflets: Pointed oval shape. Appearance: Dull to semi-glossy, smooth texture with serrated edge; serration is single and small in size. Color (top side): Near to Green Group RHS 137B. Color (bottom side): Whitish green. Stipules: Small and bearded. Other foliage characteristics: New foliage is reddish in color.

FLOWERS

Borne: Several together in clusters that open simultaneously.
Number of flowers per stem: 3 to 12 flowers.
Quantity of blooms: Continuous blooming habit.
Buds:

*Peduncle length.*—Short, 5 to 7 cm.

*Penducle surface.*—Smooth with occasionally fine hairs.

*Peduncle strength.*—Stiff and erect.

*Bud shape.*—Short, pointed ovoid.

*Bud color.*—When sepals first divide, bud color is White Group 155B. When half blown, the uppersides of the petals are White Group 155B; and the lowersides of the petals are White Group 155B.

*Receptacle color.*—near Green Group 138A.

*Receptacle shape.*—Funnel.

*Receptacle surface.*—Smooth.

*Sepals color.*—Near Green Group 138A with reddish tips.

*Sepals surface texture.*—Covered with very fine hairs: there are 1 to 3 lightly appendaged sepals and 2 unappendaged sepals.

*Blooms.*—Size: Small, with average open size of 5½ cm. Petalage: Number: 25 to 35 per flower. Length: About 2½ to 3 cm. Texture: Thick. Shape: Deltoid with slight recurved tips; when the flower first opens, it has a high center which is retained; outer petals curl back with some quilling; petal arrangement is imbricated, with few petaloids in center. Color: Upperside: White Group RHS 155B. Underside: White Group RHS 155B; the color of the base of petals intensifies to a very small greenish-yellow area at the point of attachment at the petal base, mainly on the upperside. The major color on the upperside is White Group RHS 155B.

Fragrance: None.
Reproductive organs:

*Anthers.*—Yellow and pink in color with many of medium size that are regularly arranged around styles, mixed with occasional petaloids. Very often there is a pink area on the White Group RHS 155B.

*Pollen.*—Yellow.

*Styles.*—Greenish-white.

*Stigma.*—Greenish-white.

Disease Resistance: The foliage exhibits typical susceptibility in De Kwakel, The Netherlands to powdery mildew under normal growing conditions. 'Schovian' is a greenhouse cut flower variety and, therefore, has not been tested for black spot or rust resistance.

I claim:

1. A new and distinct variety of rose plant named 'Schovian,' as illustrated and described.

* * * * *

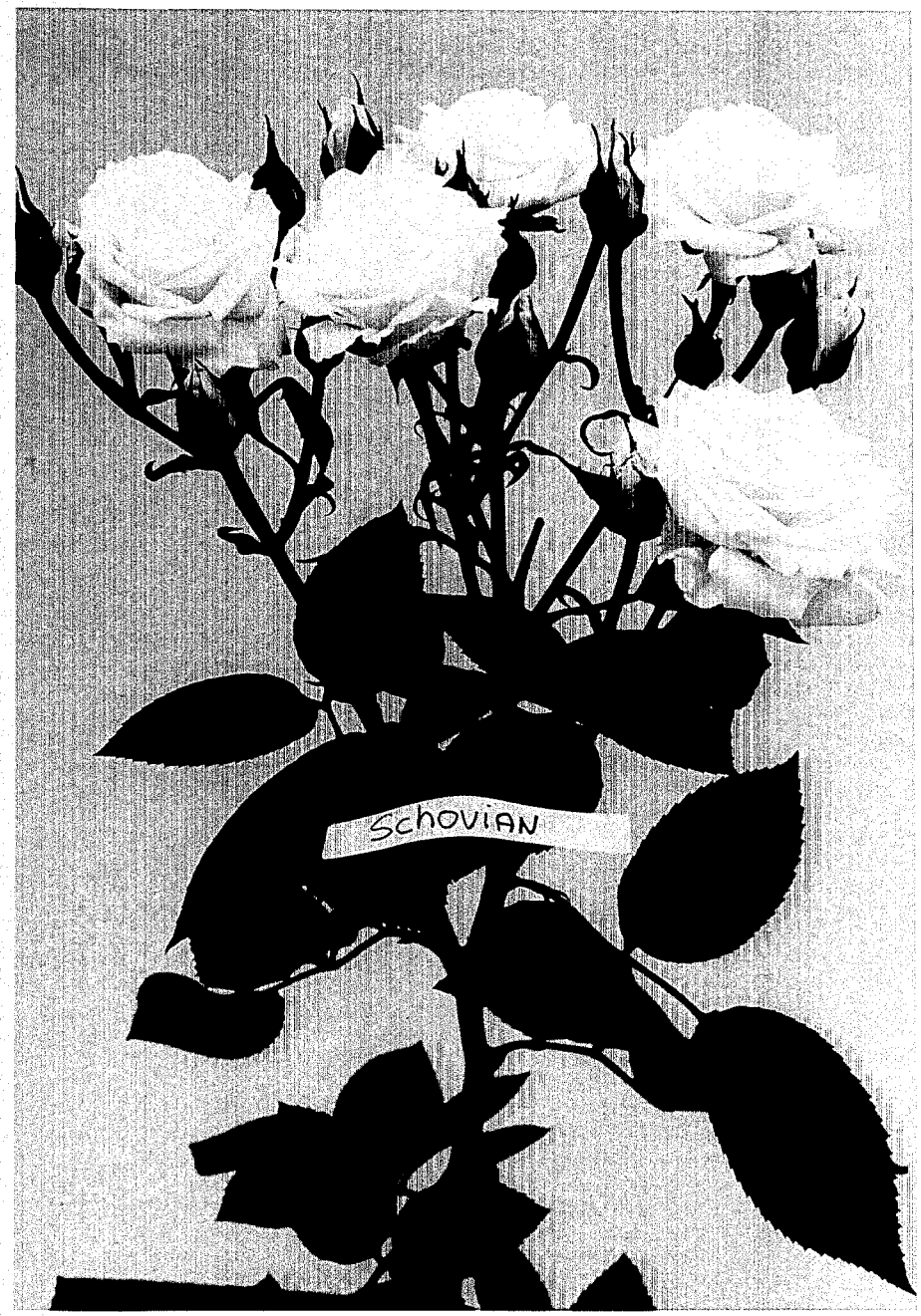
SCHOVIAN

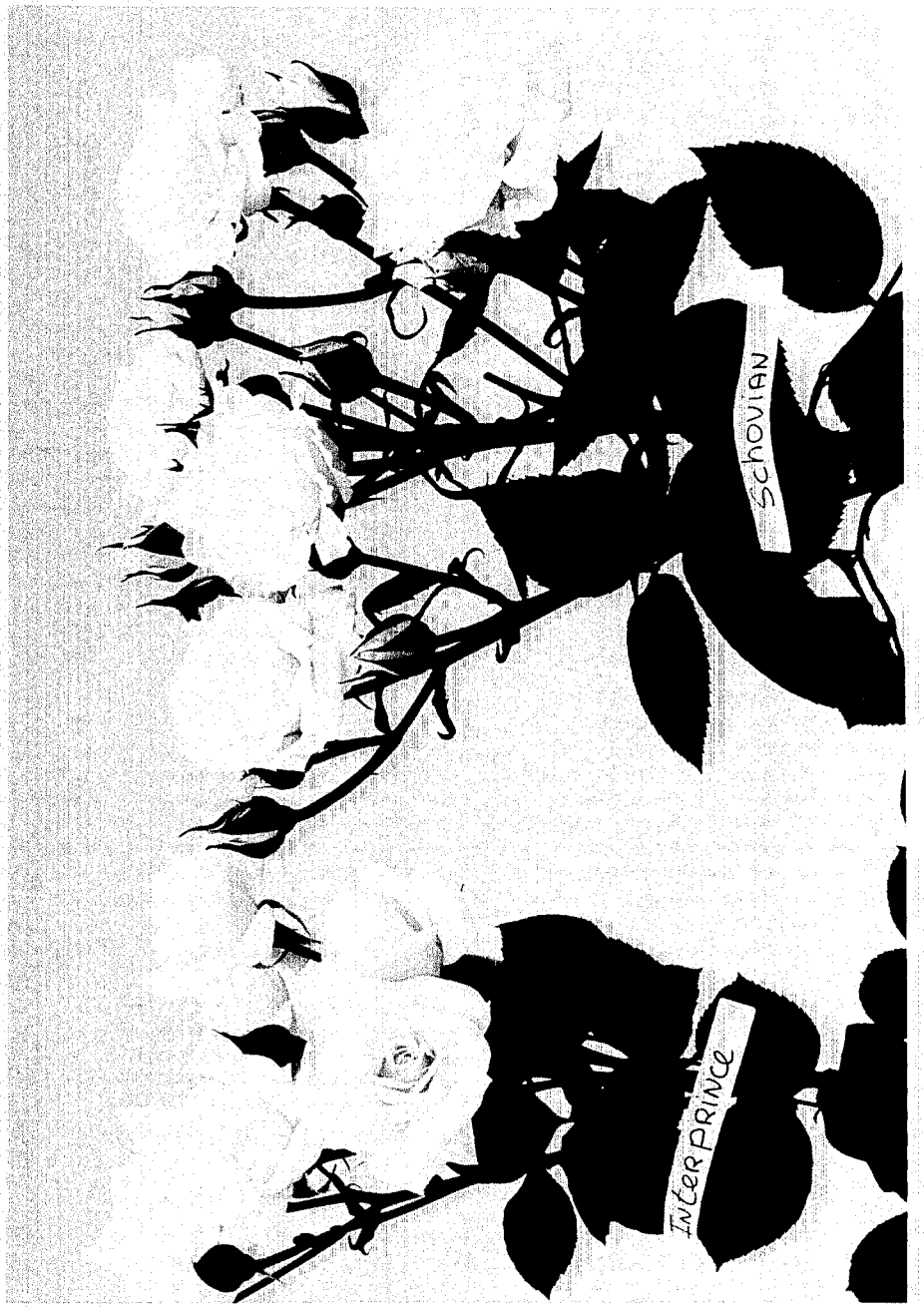
INTERPRINCE
SCHOVIAN

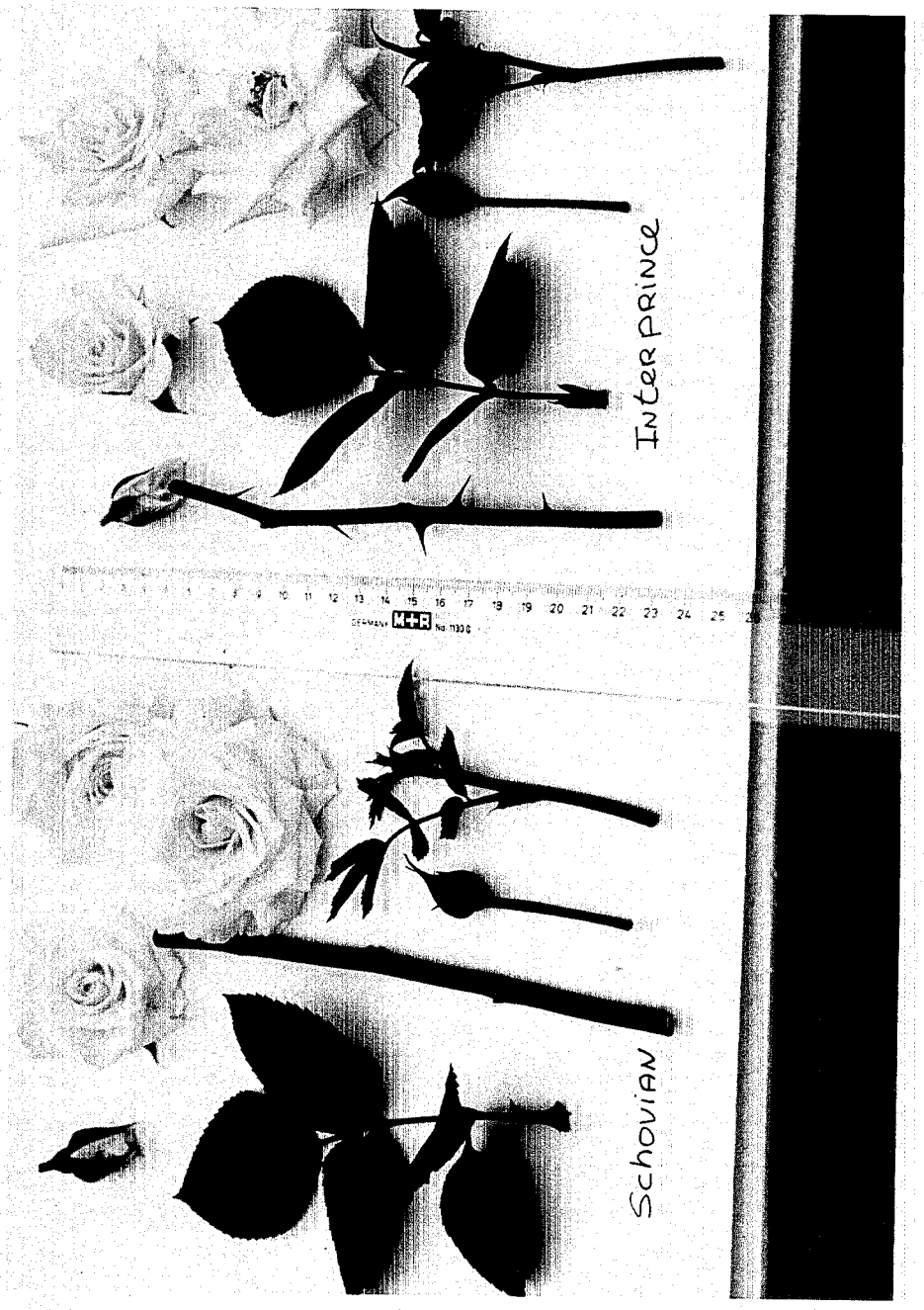
Schovian
Inter prince

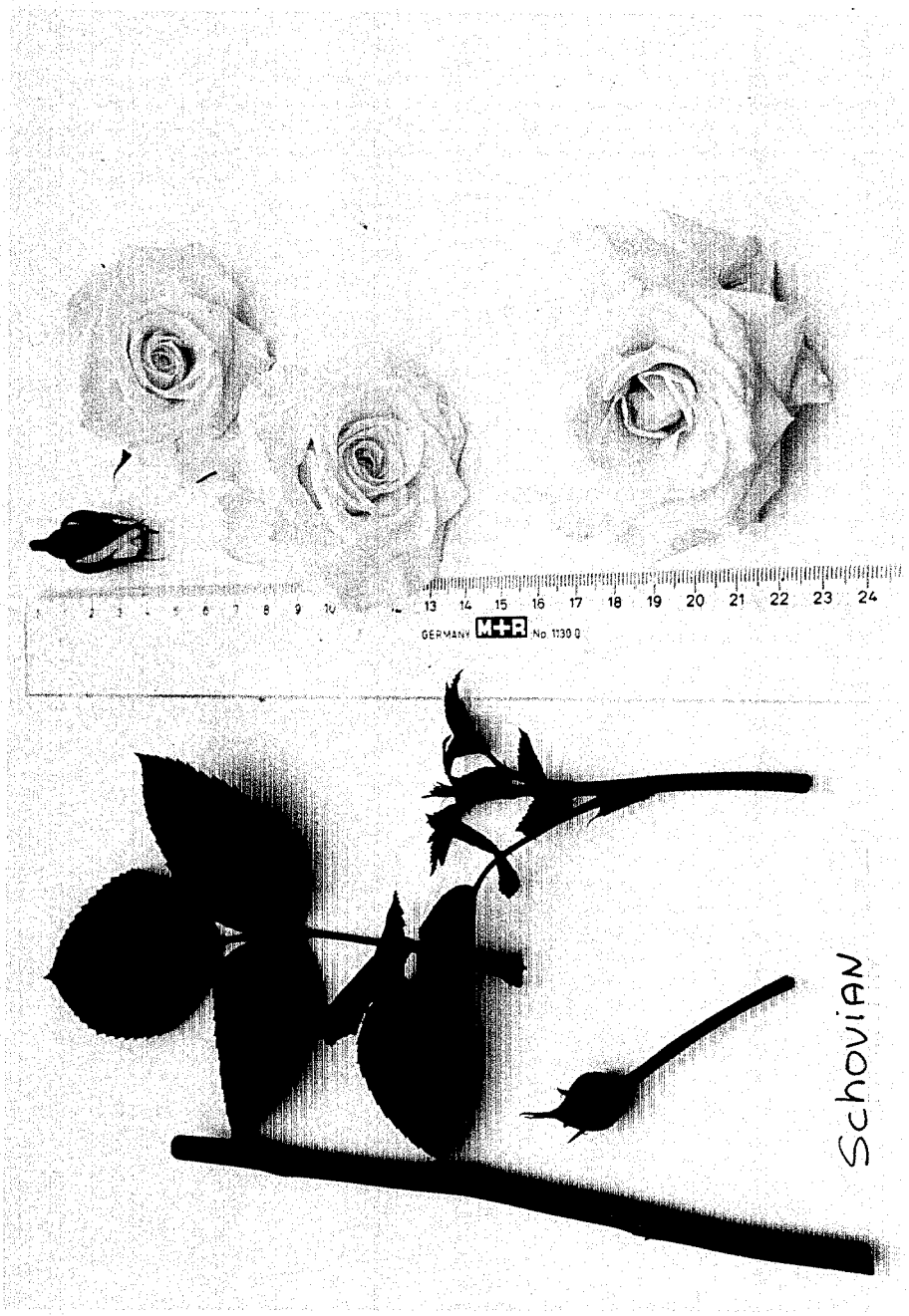
13 14 15 16 17 18 19 20 21 22 23 24
GERMANY M+R No. 1130 Q
Schovian